US007914809B2

(12) United States Patent
Atanasoska et al.

(10) Patent No.: US 7,914,809 B2
(45) Date of Patent: *Mar. 29, 2011

(54) LUBRICIOUS COMPOSITES FOR MEDICAL DEVICES

(75) Inventors: Liliana Atanasoska, Edina, MN (US); Robert Warner, Woodbury, MN (US); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1132 days.

This patent is subject to a terminal disclaimer.

(21) Appl. No.: 11/213,177

(22) Filed: Aug. 26, 2005

(65) Prior Publication Data

US 2007/0048348 A1 Mar. 1, 2007

(51) Int. Cl.
*A61F 2/06* (2006.01)
(52) U.S. Cl. ...................................... 424/423; 623/1.11
(58) Field of Classification Search .................... None
See application file for complete search history.

(56) References Cited

U.S. PATENT DOCUMENTS

| | | | |
|---|---|---|---|
| 2,993,925 A | 7/1961 | Husted | 260/448.8 |
| 3,491,134 A | 1/1970 | Seil et al. | 260/448.8 |
| 4,652,663 A | 3/1987 | Takago et al. | 549/215 |
| 5,250,322 A | 10/1993 | Takahashi et al. | 427/226 |
| 5,459,198 A | 10/1995 | Sharp | 525/102 |
| 5,588,443 A | 12/1996 | Davidson | 128/772 |
| 5,726,247 A | 3/1998 | Michalczyk et al. | 525/102 |
| 5,808,125 A | 9/1998 | Standke et al. | 556/424 |
| 5,849,942 A | 12/1998 | Standke et al. | 556/424 |
| 5,863,509 A | 1/1999 | Standke et al. | 427/221 |
| 5,876,686 A | 3/1999 | Michalczyk et al. | 423/592 |
| 6,054,601 A | 4/2000 | Standke et al. | 556/425 |
| 6,113,579 A | 9/2000 | Eidenschink et al. | 604/264 |
| 6,177,582 B1 | 1/2001 | Jenkner et al. | 556/425 |
| 6,228,936 B1 | 5/2001 | Standke et al. | 524/838 |
| 6,251,989 B1 | 6/2001 | Edelmann et al. | 524/837 |
| 6,288,256 B1 | 9/2001 | Standke et al. | 556/425 |
| 6,491,838 B1 | 12/2002 | Standke et al. | 252/8.57 |
| 6,514,228 B1 | 2/2003 | Hamilton et al. | 604/96.01 |
| 6,517,515 B1 | 2/2003 | Eidenschink | 604/101.05 |
| 6,545,097 B2 | 4/2003 | Pinchuk et al. | 525/240 |
| 6,589,546 B2 * | 7/2003 | Kamath et al. | 424/423 |
| 6,713,186 B1 | 3/2004 | Jenkner et al. | 428/447 |
| 6,855,770 B2 | 2/2005 | Pinchuk et al. | 525/240 |
| 2003/0027020 A1 | 2/2003 | Berg et al. | 428/702 |
| 2004/0019143 A1 * | 1/2004 | Koloski et al. | 524/434 |
| 2004/0215169 A1 | 10/2004 | Li | 604/537 |
| 2006/0230476 A1 * | 10/2006 | Atanasoska et al. | 977/933 |

FOREIGN PATENT DOCUMENTS

WO WO 2004/005533 * 7/2003

OTHER PUBLICATIONS

Kim et al. Effect of fluoridation of hydroxyapatite in hydroxyapatite-polycaprolactone composites on osteoblast activity, Biomaterials 26 (2005) 4395-4404.*

Kim et al. Effect of fluoridation of hydroxyapatite-polycaprolactone composites on osteoblast activity, Biomaterials 26 (2005) 4395-4404.*
Gu et al. Preparation and characterization of hydrophobic organic-inorganic composite thin films of PMMA/SiO2/TiO2 with low friction coefficient Applied Science 221(2004) 129-135.*
Mahltig et al. (J. sol-gel sci. and tech. 27, 43-52, 2003.*
Degussa (Dynasylan Product info).*
Brinker, Scherer et al.: "Sol-Gel Science", Academic Press, San Diego 1990, for the basics of sol formation, p. 2-15.
Ameduri, Bruno, et al., "Hybrid Organic-Inorganic Gels Containing Perfluoro-Alkyl Moieties," *Journal of Fluorine Chemistry*, 104 (2000) 185-194.
Cachet et al., "Tin Dioxide Thin Films Prepared From AA New Alkoxyfluorotin Complex Including A Covalent Sn-F Bond" *Thin Solid Films*, 388 (2001) 41-49.
Campostrini et al., "Sol-Gel Synthesis and Pyrolysis Study of Oxyfluoride Silica Gels" *Journal of Sol-Gel Science and Technology*, 23 (2002) 107-117.
Campostrini et al, "Pyrolysis Study of Fluorinated Sol-Gel Silica" *Journal of Thermal Analysis and Calorimetryl*, vol. 78 (2004) 657-677.
Degussa, "Innovative Sol-Gel Coatings with Silvento Silanes", (Jul. 2003).
Gill et al., "Bioencapsulation Within Synthetic Polymers (Part I): Sol-Gel Encapsulated Biologicals," *Tibtech*, 18 (2000) 282-296.
Gu, Guotuan, et al., "Preparation and Characterization of Hydrophobic Organic-Inorganic Composite Thin Films of PMMA/SiO2/TiO2 with Low Friction Coefficient," *Applied Surface Science*, 221 (2004) 129-135.
Gu et al., "Hydrophobic Inorgani-Organic Thin Films Wit a Low Coefficient of Friction" *Materials Research Bulletin*, 39 (2004) 1037-1044.
Han Chi Hwan et al., "Nanocrystalline F-doped Tin Dioxide Materials: Texture, Morphology, and Photosensitization With A Perylene-Substituted Organetin" *Journal of Fluorine Chemistry*, 125 (2004) 1247-1254.
Kang et al., "Fabrication of Characterstics of Sol-Gel Derived Fluorinated Hybrid Material Films" *Journal of Sol-Gel Science and Technology*, 31 (2004) 113-116.
Kamitani and Teranishi, "Development of Water-Repellent Glass Improved Water-Sliding Property and Durability" *Journal of Sol-Gel Science and Technology*, 26 (2003) 823-825.
Kawase, Tokuzo, et al., "End-Capped Fluoroalkyl-Functional Silanes. Part I: Modification of Glass", *J. Adhesion Sci. Technol.*, vol. 16, No. 8, pp. 1103-1120 (2002).
Kawase, Tokuzo, Et al., "End-Capped Fluoroalkyl-Functional Silanes. Part II: Modification of Polymers and Possibility of Multifunctional Silanes", *J. Adhesion Sci. Technol.*, vol. 16, No. 8, pp. 1121-1140 (2002).
Kickelbick, G., "Concepts for the Incorporation of Inorganic Building Blocks Into Organic Polymers on a Nanoscale", *Prog. Polym. Sci.*, 28 (2003) 83-114.

(Continued)

*Primary Examiner* — Robert A Wax
*Assistant Examiner* — Danah Al-Awadi
(74) *Attorney, Agent, or Firm* — Vidas, Arrett & Steinkraus, P.A.

(57) ABSTRACT

A medical device having at least one composite region thereon formed of composite material comprising a polymer and a fluorinated sol-gel derived ceramic. The composite material is useful as a coating material for imparting a low coefficient of friction to a substrate.

28 Claims, 5 Drawing Sheets

OTHER PUBLICATIONS

Kim, Jae-Pil, et al., "Hydrolysis and Condensation of Fluorine Containing Organosilicon", *Optical Materials*, 21 (2002) 445-450.

Mahltig and Bottcher, "Modified Silica Sol Coatings for Water-Repellent Textiles" *Journal of Sol-Gel Science and Technology*, 27 (2003) 43-52.

Monde, Takashi, et al., "Preparation and Surface Properties of Silica-Gel Coating Films Containing Branched-Polyfluoroalkylsilane", *Journal of Non-Crystalline Solids*, 246 (1999) 54-64.

Nishikawa, T. et al., "A New Approach to Molecular Devices Using SAMs, LSMCD and Cat-CVD", *Science and Technology of Advanced Materials*, 4 (2003) 81-89.

Nolan, Benjamin et al., "New Synthesis of Polyfluorodiols: Nine New Derivatives of HOC(2-OH-C6H4)(CF3)2" *Journal of Fluorine Chemistry*, 118 (2002) 103-106.

Poncelet et al., "Fluoroalkoxides As Molecular Precursors of Fluoride Materials By the Sol-Gel Process," *Journal of Sol-Gel Science of Technology*, 13, 129-132 (1998).

Satoh, K. et al., "Preparation of Super-Water-Repellent Fluorinated Inorganic-Organic Coating Films on Nylon 66 by the Sol-Gel Method Using Microphase Separation", *Journal of Sol-Gel Science and Technology*, 27 (2003) 327-332.

Shang et al., "Optically Transparent Superhydrophobic Silica-Based Filmes", *Thin Solid Films*, Article in Press, (2004).

Shao, Hui, et al., "Synthesis and Surface Antimicrobial Activity of a Novel Perfluorooctylated Quaternary Ammonium Silane Coupling Agent", *Journal of Fluorine Chemistry*, 125 (2004) 721-724.

Tae et al., "Sustained Release of Human Growth Hormone From In Situ Forming Hydrogels Using Self-Assembly of Fluoroalkyl Ended Poly(ethylene glycol)," *Biomaterials*, 26 (2005) 5259-5266.

Yun, Chi et al., "Alkaline-Earth Metal Fluoroalkoxide Complexes with Multi-Coordinated Polyether Appendage: Synthesis and Characterization", *Inorganica Chimica Acta* 334, 172-182 (2002).

Yun Chi et al., "Preparation and Characterization of Volatile Alkaline-Earth Metal Complexes With Multiply Coordinated Aminoalkoxide Legands," *The Royal Society of Chemistry*, 2001, 2462-2466.

http://www.psre.usm.edu/mauritz/solgel.html, (Feb. 2001).

* cited by examiner

LUBRICIOUS COMPOSITES FOR MEDICAL DEVICES

FIELD OF THE INVENTION

Catheter assemblies, such as balloon catheter assemblies, are used for a variety of applications including delivery of medical devices such as stent delivery, for percutaneous transluminal coronary angioplasty (PTCA), cutting balloon catheters for recanalizing and dilating a diseased vessel and facilitating balloon angioplasty procedures, and so forth.

PTCA is a widely used procedure for the treatment of coronary heart disease. In PTCA the balloon catheter is used to restore free flow in a clogged coronary vessel. The catheter is maneuvered through the patient's vasculature and into the patient's coronary anatomy until the balloon is properly positioned across the stenosis to be dilated. This involves a torturous path with very little room inside the vessel. Once properly positioned, the balloon is inflated within the stenotic region of the artery one or more times to a predetermined size to reopen the coronary passageway and increase the blood flow therethrough.

Balloon catheters generally comprise an elongated shaft with an inflatable balloon on the distal end of the shaft. An inflation lumen extending within the shaft is used to deliver inflation fluid to the balloon interior. In over the wire or rapid exchange designs, a guide wire is slidably received within a guide wire lumen extending at least within a distal section of the catheter.

A lubricious coating may be provided on the outer surface of the catheter shaft to facilitate the movement of the catheter within the patient's body lumen. Additionally, a lubricious coating may be provided on an inner surface of the shaft which defines the guide wire lumen, to facilitate the movement of a guide wire therein. The lubricious coatings often comprise silicone or hydrophilic polymeric materials which become lubricious after absorbing water.

One problem, which may occur with lubricious coatings have high lubricity, is poor adhesion to the catheter shaft surface. Other challenges include providing high lubricity without a loss of other catheter shaft characteristics such as low profile, strength, flexibility, and ease of manufacture.

One method employed to improve adhesion of lubricious coatings has been to apply a tie layer over the base material, and then apply a lubricious material over the tie layer. This process decreases manufacturing efficiency.

One material commonly used to provide a low friction surface is polytetrafluoroethylene (PTFE). However, because of its very low coefficient of friction, it is difficult to wet out the surface of PTFE. Consequently, it can be difficult to adhere other polymers to PTFE, making it difficult to use as a low friction coating. Furthermore, PTFE is very difficult to process.

There remains a need for an improved lubricious surface which provides the catheter shaft with a desirable combination of properties such as good pushability and kink resistance, and a low profile.

SUMMARY OF THE INVENTION

In one aspect, the present invention relates to implantable or insertable medical devices, at least a portion of which contain or include one or more composite regions. These composite regions, in turn, are formed of a hybrid organic-inorganic material that includes a combination of polymer and fluorinated sol-gel derived ceramic.

In one aspect, the composite region includes a coating of a composite material that includes a combination of a polymer and a fluorinated sol-gel derived ceramic. In one embodiment, fluoroalkylsilanes are employed to produce a fluorinated sol-gel ceramic.

In another aspect, the present invention relates to a method of providing lubricity to the surface of a medical device, the method including the steps of forming a composition comprising a polymer and a hydrolyzed and partially condensed fluorinated sol-gel ceramic precursor, and applying said composition to the surface of the medical device, and further condensing the hydrolyzed, partially condensed ceramic precursor to form a hybrid inorganic-organic fluorinated sol-gel composite on the surface of the device.

Application of the polymer/fluorinated sol-gel ceramic composite described herein to the surface of a medical device can decrease the coefficient of friction of the device surface, thereby improving the lubricity of the device surface, without negatively impacting the bulk properties of the device material.

Thus, the medical devices made according to the invention, not only have the enhanced mechanical characteristics, including enhanced strength, toughness and/or abrasion resistance, provided by the coating, but also have lubricity.

The present invention can be employed in combination with any medical device including, but not limited to, catheter assemblies, medical balloons, stents, grafts, stent-grafts, embolization devices, vena-cava filters, etc.

These and other aspects, embodiments and advantages of the present invention will become immediately apparent to those of ordinary skill in the art upon review of the Detailed Description and claims to follow.

DETAILED DESCRIPTIONS OF THE INVENTION

Figure 1:
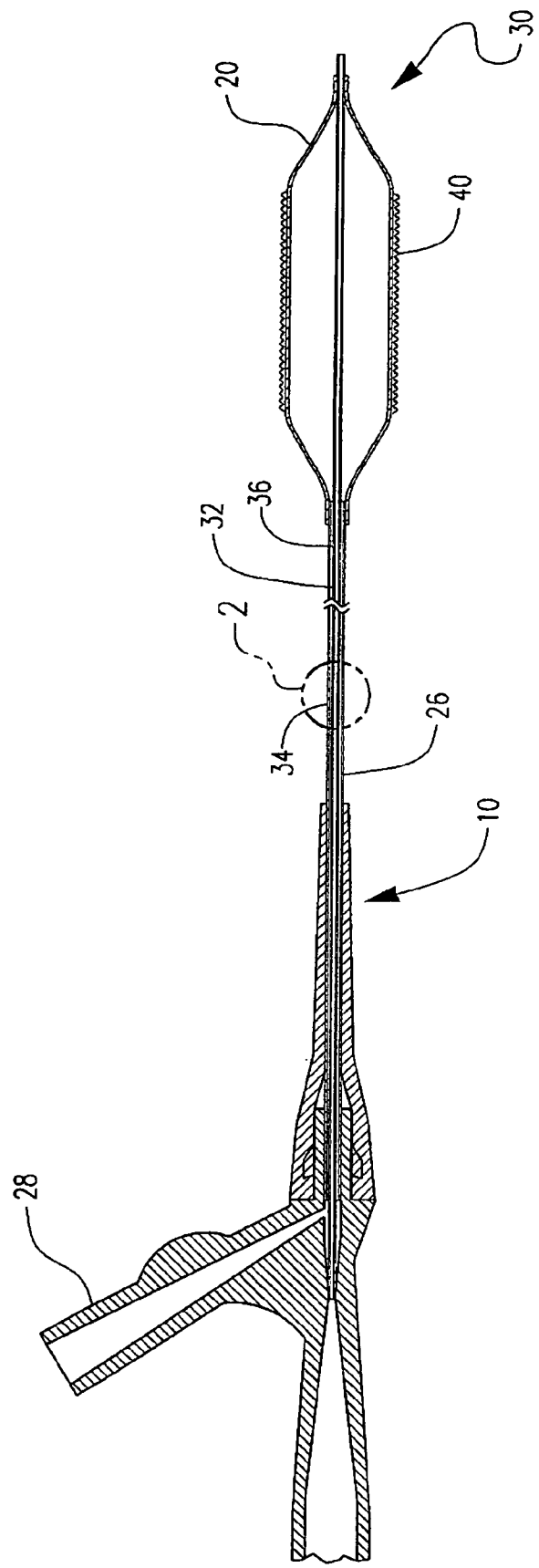
FIG. 1 is a longitudinal cross-sectional view of an example of a catheter assembly in which a polymer/fluorinated sol-gel ceramic composite material is employed on the inner surface of an inner shaft.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

In one aspect, the present invention provides implantable or insertable medical devices containing or including one or more composite regions, which contain or include a hybrid organic-inorganic material that comprises polymer and ceramic, wherein the ceramic is a fluorinated sol-gel derived ceramic. The composite regions provide several advantages including enhanced mechanical characteristics including enhanced strength, toughness and abrasion resistance, as well as a lubricious surface provided by fluorocarbon groups of the ceramic.

The present invention is suitable for use in combination with any medical devices used for a variety of medical procedures in which such devices are inserted or implanted. Examples of such devices include, but are not limited to, balloons, catheters (e.g., renal or vascular catheters such as balloon catheters, guide catheters), stent delivery systems, guide wires, needles, surgical instruments, endoscopic equipment, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, wound drains, gastroenteric tubes, urethral inserts, laproscopic equipments, pacemaker leads, defibrillator leads, shunts such as arteriovenuous shunts, as well as various other medical devices that are adapted for implantation or insertion into the body.

The medical devices of the present invention include implantable and insertable medical devices that are used for diagnosis, for systemic treatment, or for the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone. As used herein, the term "diagnosis" refers to the act or process of determining the nature of a disease, condition or injury through examination of a patient. As used herein, "treatment" refers to the prevention of a disease or condition, the reduction or elimination of symptoms associated with a disease, condition or injury, or the substantial or complete elimination of a disease, condition or injury. Typical subjects (also referred to as "patients") are vertebrate subjects, more typically mammalian subjects and even more typically human subjects.

FIG. 1 is a longitudinal cross-sectional view of an example of a catheter assembly 10 in which a polymer/fluorinated sol-gel ceramic composite material can be employed on at least the inner surface of an inner shaft in order to reduce the wire-movement friction when a guide-wire (not shown) is inserted through the lumen defined by the inner surface of the inner shaft. Catheter assembly 10 is representative of a simple over-the-wire (OTW) or single-operator-exchange (SOE) angioplasty balloon catheter according to the invention. Such balloon catheters are discussed, for example, in commonly assigned U.S. Pat. Nos. 6,113,579, 6,517,515 and 6,514,228, each of which is incorporated by reference herein in its entirety. In this embodiment, catheter 10 has an elongate shaft assembly 26 and a conventional OTW-type manifold assembly 28 connected to proximal end of shaft assembly 26. Manifold assembly 28, is further shown with a strain relief 30. The shaft assembly 26 includes an outer tube 34 coaxially disposed about inner tube 32 which defines a guide wire lumen 36 as shown in enlarged view in FIG. 2, taken at section 2 in FIG. 1. This is only an illustration of such a catheter assembly and is not intended to limit the scope of the present invention. Numerous structures are known to those of skill in the art, any of which may be employed herein.

Figure 2:
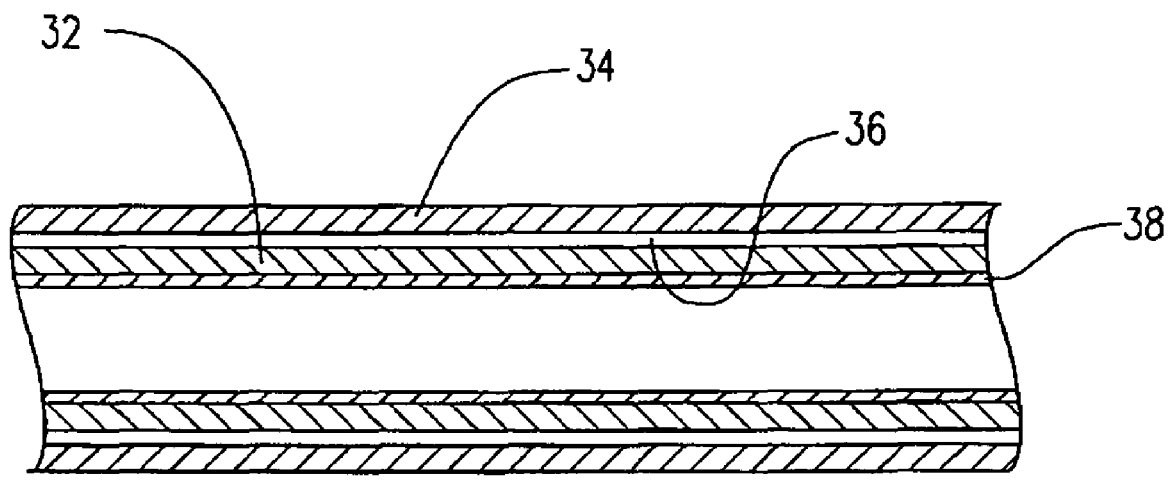
FIG. 2 is an enlarged longitudinal cross-sectional view taken at section 2 in FIG. 1.

As can be seen more clearly in FIG. 2, an enlarged longitudinal cross-sectional view taken at section 2 in FIG. 1, the polymer/fluorinated sol-gel ceramic composite material 38 is deposited on the inner surface of the guide wire lumen.

The polymer/fluorinated sol-gel ceramic composite material 38 according to the invention may also improve balloon durability and abrasion resistance, in addition to providing lubricity to the balloon surface.

Figure 3:
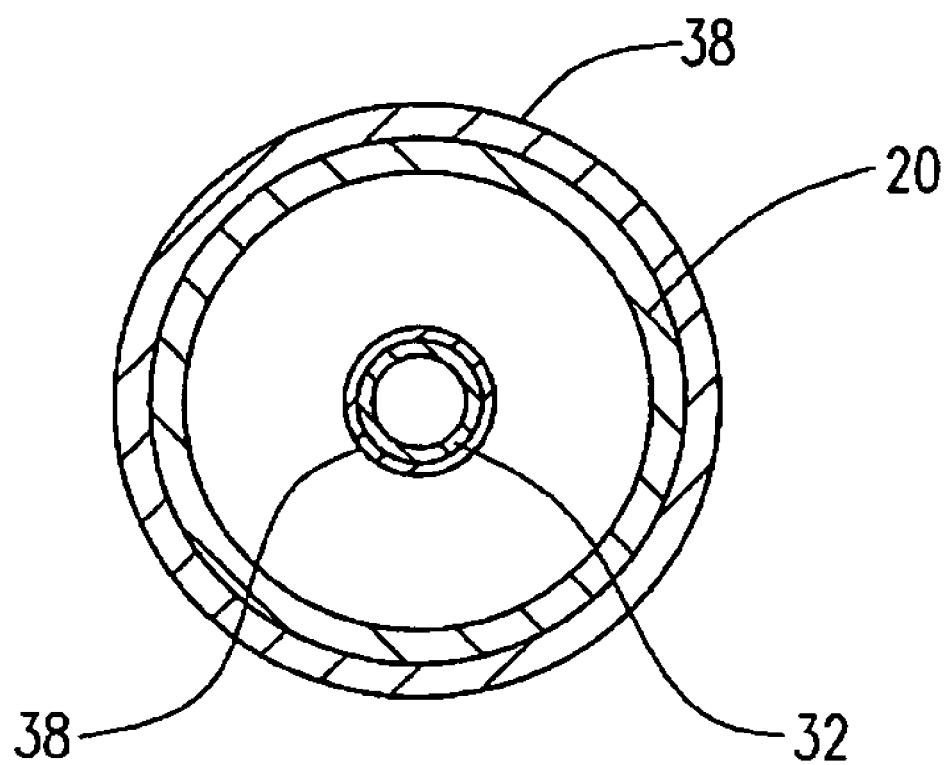
FIG. 3 is a radial cross-sectional view of a balloon taken at section 3 in FIG. 1.

FIG. 3 is a radial cross-sectional view through balloon 20 of catheter assembly 10. Balloon 20 has a polymer/fluorinated sol-gel ceramic composite material 38 deposited on the outer surface. The inner shaft 32 having fluorinated sol-gel ceramic composite material 38 deposited on the inner surface of inner shaft 32 can also be seen in radial cross-section in FIG. 3.

Figure 4:
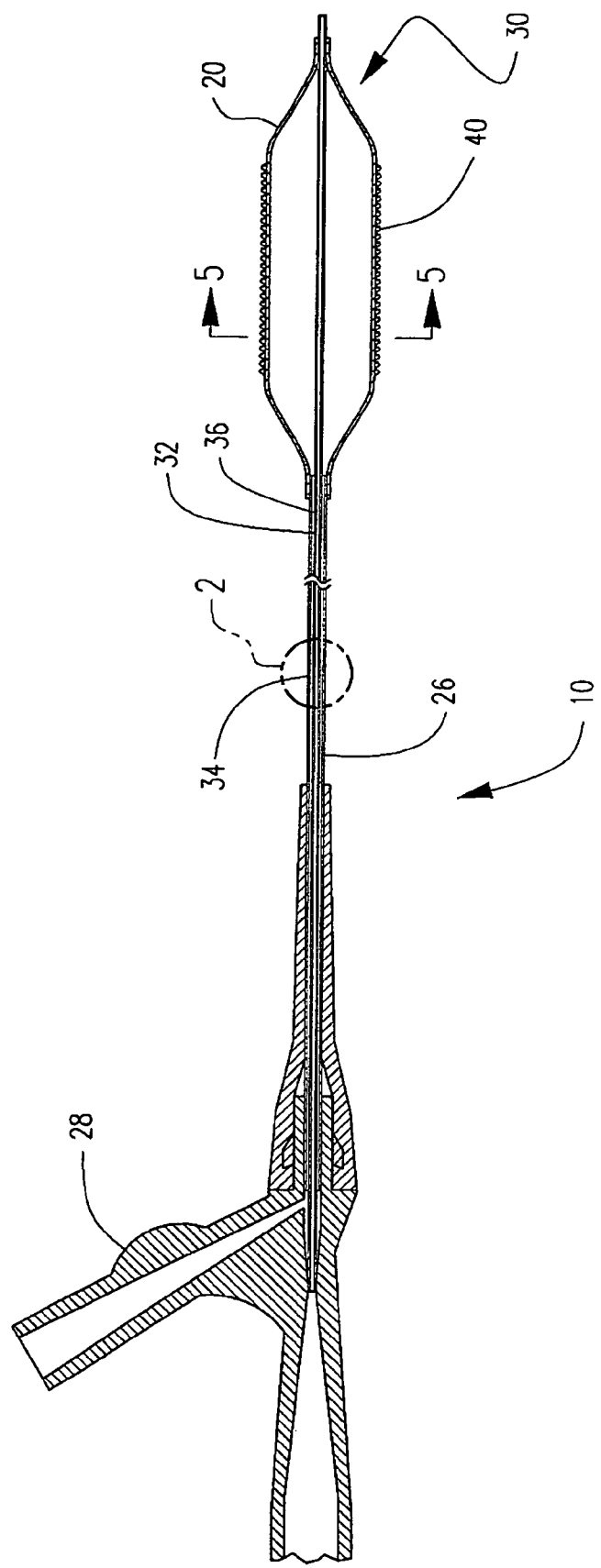
FIG. 4 is a longitudinal cross-sectional view of a catheter assembly similar to that shown in FIG. 1 further in combination with a stent.
Figure 5:
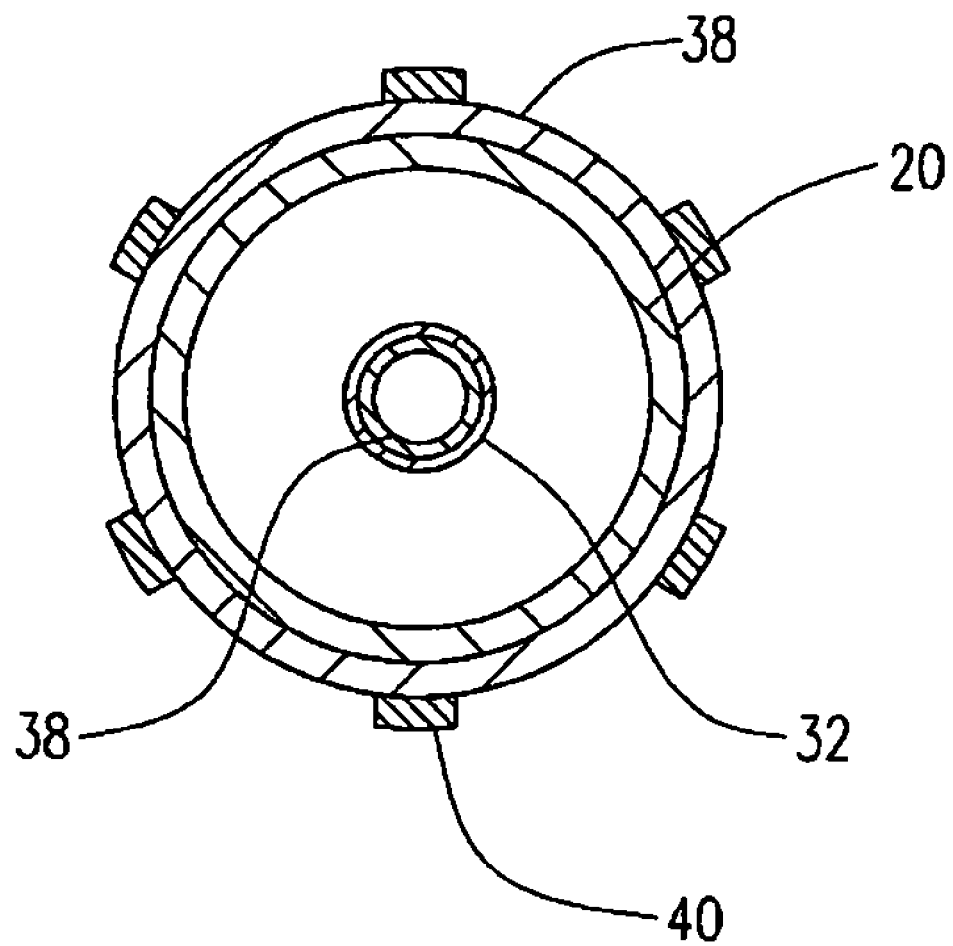
FIG. 5 is a radial cross-sectional view taken at section 4 in FIG. 4.

FIG. 4 is a longitudinal cross-sectional view of a catheter assembly 10 similar to that shown in FIG. 1, but further shown in combination with a stent 40. Polymer/fluorinated sol-gel ceramic composite is shown deposited on balloon 20. During deployment, the balloon is inflated, thus expanding the stent at the lesion site. The fluorinated sol-gel ceramic composite can improve balloon withdrawal after the stent has been deployed and the balloon deflated by decreasing the coefficient of friction of the balloon surface. FIG. 5 is a radial cross-sectional view taken at section 4 in FIG. 4.

As discussed above, the composite regions according to the present invention contain or include a hybrid material that is a composite of polymer and ceramic, and the ceramic is a fluorinated sol-gel derived ceramic.

The fluorinated sol-gel materials used in the invention can be made using any known sol-gel techniques. Basic hybrid inorganic-organic sol-gel derived ceramic materials for use in medical devices are disclosed in commonly assigned copending U.S. patent application Ser. No. 11/094,638, filed Mar. 30, 2005, the entire content of which is incorporated herein by reference.

As described therein, the ceramic portion of a polymer/fluorinated sol-gel derived ceramic composite material is typically a network of metal or semi-metal oxides or mixed oxide compounds. The ceramic is suitably formed using sol-gel techniques. In a typical sol-gel process, sol-gel precursors such as inorganic metal salts or metal organic compounds such as metal alkoxides are subjected to a series of hydrolysis and polymerization reactions to form a colloid. The colloid is then further condensed to form a gel. The process may be acid or base catalyzed which is discussed in more detail below.

Examples of metal or semi-metal oxides include, but are not limited to, silicon, zirconium, titanium, aluminum, tin, hafnium, tantalum, molybdenum, tungsten, rhenium and/or iridium oxides, among others. In general, metal/semi-metal atoms (designated generally herein as M) within the ceramic phases are linked to one another via covalent linkages, such as M-O-M linkages, although other interactions are also commonly present including, for example, hydrogen bonding due to the presence of hydroxyl groups such as residual M-OH groups within the ceramic phases.

The sol-gel ceramic phase according to the invention can also be formed by hydrolysis of metal fluoroalkoxides such as alkaline earth metal fluoroalkoxides.

The technique typically starts with a precursor material which may be an inorganic metallic salts or semi-metallic salts, metallic or semi-metallic complexes/chelates such as metal acetylacetonate complexes, metallic or semi-metallic hydroxides, organometallic and organo-semi-metallic compounds such as metal alkoxides, silicon alkoxides and acyloxides, etc.

Silicon alkoxides and acyloxides are beneficial due to the variety of formulation options, including co-condensation with related compounds having strong stable C—Si bonds and which can form a strong link between the polymeric and ceramic networks. However, as an alternative to alkoxy or acyloxy groups other known hydrolyzable groups may be employed on the silicon or metal precursor compounds that are condensed to form the sol-gel ceramic.

In general, the sol-gel process involves the transition of a system from a liquid "sol" (mostly colloidal) into a solid "gel" phase. In a typical sol-gel process, precursor materials such as those described above are subjected to hydrolysis and condensation reactions to form a colloidal suspension, or "sol". One or more precursor materials may first react in the presence of water in a process called hydrolysis. The product of the hydrolysis reaction, then condense, forming a network of inorganic nanoparticles. When the sol is applied to substrate, the particles condense further forming a gel. See C. J. Brinker; G. W. Scherer: "Sol-Gel Science", Academic Press, San Diego 1990, for the basics of sol formation.

Any suitable network forming metal alkoxide may be employed in the formation of the sol-gel ceramic. For example, an alkoxide of choice (such as a methoxide, ethoxide, isopropoxide, tert-butoxide, etc.) of a semi-metal or metal of choice (such as silicon, aluminum, zirconium, titanium, tin, hafnium, tantalum, molybdenum, tungsten, rhenium, iridium, etc.) may be dissolved in a suitable solvent, for example, in one or more alcohols, or other polar, protic or aprotic solvents, such as tetrahydrofuran, dioxane, dimethylformamide or butyl glycol, for example, may be employed. Suitable alcohols include, but are not limited to, ethanol, butanol, propanol, isopropanol, cyclohexanol, etc.

As discussed above, in some processes, fluorinated solvents, such as fluorinated hydrocarbons or fluorohydrocarbons can be employed.

Subsequently, a sol is formed, by hydrolysis/condensation reactions or by other condensation mechanisms. If desired, additional agents can be added, such as agents to control the viscosity and/or surface tension of the sol. For example, formamide or oxalic acid may reduce the surface tension. Such agents are known in the art. As a final stage the sol is converted to a gel by driving the condensation reaction further, for instance by drying the composition.

A simplified scheme of a ceramic network forming process is represented below (from G. Kickelbick, "Concepts for the incorporation of inorganic building blocks into organic polymers on a nanoscale" *Prog. Polym. Sci.*, 28 (2003) 83-114, the entire disclosure of which is incorporated herein by reference):

Hydrolysis:

$$M(OR)_n \xrightarrow{H_2O} M(OR)_{n-m}(OH)_m + HOR$$

Condensation:

$$2\, M(OR)_{n-m}(OH)_m \xrightarrow{H_2O}$$

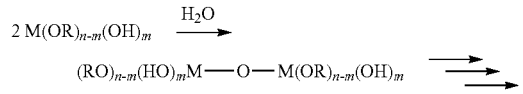

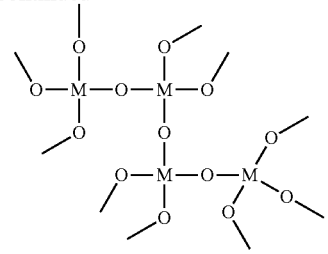

M = Si, Ti, Zr, Sn, Al, ...
R = Me, Et, $^i$Pr, $^n$Pr, $^n$Bu, $^t$Bu, ...

In general, R may be a hydrocarbon group, suitably an alkyl group of from 1-20 carbon atoms which optionally may be interrupted with one or more ether oxygen atoms, or an acyl group, for instance formyl, acetyl or benzoyl. Further, n is suitably equal to a valence of M and m is a positive number between 0 and n.

Hydrolysis can occur without the addition of a catalyst. However, hydrolysis is most rapid and complete when a catalyst is added. Useful catalysts include, but are not limited to, mineral acids such as hydrochloric acid (HCl), carboxylic acids such as acetic acid and derivatives thereof such as trifluoroacetic acid, ammonia, potassium hydroxide (KOH), amines, hydrogen fluoride (HF), potassium fluoride (KF), etc. Furthermore, the rate and completion of the hydrolysis reaction is influenced to a greater degree by the strength and concentration of the acid or base employed.

The present invention employs sol-gel derived composite materials in which at least some of the ceramic precursor materials have carbon-linked fluorocarbon groups to provide the medical device with a lower coefficient of friction while maintaining abrasion resistance and durability of the medical device surface, and without altering other bulk properties.

Any suitable hydrolysable net-work forming metal compound may be employed herein, providing that at least some of the molecules also have at least one fluorohydrocarbon group-metal atom link or bond which is not subject to hydrolysis, or at least subject only to partial hydrolysis. Suitably, the at least one fluorohydrocarbon group is a perfluorocarbyl segment.

Suitable metals which may be employed in ceramic precursor material suitable for formation of the fluorinated networks include, but are not limited to, aluminum (Al), silicon (Si), boron (B), tin (Sn), titanium (Ti), zirconium (Zi), hafnium (Hf), tantalum (Ta), molybdenum (Mo), tungsten (W), rhenium (Re), iridium (Ir), etc. The alkaline earth metals such as strontium (Sr) and barium (ba) and the rare earth lanthanide series may be employed in some embodiments.

Each ceramic precursor molecule preferably has at least two, and more preferably three network-forming groups. These network forming groups are typically linked through hydrolysable bonds such as alkoxy, acyloxy, carboxy, chlorine and nitrogen, for example.

For example, aluminum and boron, each have three valence electrons, has at least one fluoroalkyl group-metal atom line or bond which is not subject to hydrolysis or at least only partial hydrolysis, and two network-forming groups.

Silicon, with four valence electrons, on the other hand, may have at least one fluroalkyl group-silicon atom link or bond which is not subject to hydrolysis, or is subject only to partial hydrolysis, and three network-forming groups, such as the alkoxy groups. Organofluorosilanes may be employed which have less than three network-forming groups, but may then be prepared as a composite using another network forming metal alkoxide such as a hydrolysable alkoxysilane, discussed in more detail below.

For a more detailed discussion, see U.S. Pat. No. 5,459,198, the entire content of which is incorporated by reference herein.

Examples of ceramic precursor molecules of this type are represented by the following general structure:

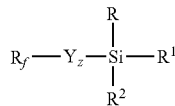

Wherein $R_f$ is a mono, oligo- or perfluorinated alkyl group having up to 18 carbon atoms or a mono-, oligo- or perfluorinated aryl group. Furthermore, $R_f$ may contain O, S, Cl or N, for example, as well, providing that if a hydrolysable group is present in $R_f$, some fluorine atoms attached to carbon are present closer to Si than the hydrolysable group, or Y is itself a mono-, oligo, or perfluorinated group. Y may be an aryl group or $CH_2$ or $CH_2CH_2$ and z may be 0 or 1. Y may also be a hydrocarbon group of a fluoroalkoxy provided it is at least partially non-hydrolyzable such that a group having fluorine atoms attached to carbon remain in the ceramic network after the hydrolysis and condensation reactions. R, $R^1$ and $R^2$ may be independently alkyl groups of 1 to about 8 carbon atoms; halogen atoms selected from chlorine, bromine and iodine; alkoxy, carboxy or acyloxy groups which are attached to silicon through hydrolysable groups, and at least two of R, $R^1$ and $R^2$ are hydrolysable groups. If two are hydrolysable, another alkoxysilane may be added as a network building molecule. One of R, $R^1$ and $R^2$ may be a fluorine containing group as well. Furthermore, other hydrolysable bonds such as a silicon-nitrogen bond, may be present, providing that at least two hydrolysable groups are present.

Another example of a hydrolysable silane having fluorine attached via a carbon-silicon bond, is as follows:

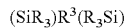

Wherein R is a hydrolysable group such as alkoxy having 1 to about 8 carbon atoms, acyloxy having 1 to about 8 carbon atoms, carboxy, or halogen, $R^3$ is a hydrocarbon linking group substituted with two or more fluorine atoms may be alkyl groups or aryl groups and a may be an integer from 4 to 10.

A specific example of a compound of this type is the following:

Similar types of molecular structures are disclosed in U.S. Pat. No. 5,459,198, the entire content of which is incorporated by reference herein.

Another method of providing carbon-linked fluorocarbon groups may be through the use of carbon-linked fluorocarbon substituted silanes, for instance fluoroalkylsilanes that also have at least one silicon-linked hydrolyzable group. Examples of suitable such fluoroalkylsilanes which may be employed include, but are not limited to, $CF_3(CH_2)_2Si(OCH_3)_3$, $CF_3(CH_2)_2SiCl_3$, $CF_3(CF_2)_5(CH_2)_2Si(OCH_3)_3$, $CF_3(CF_3(CF_2)_5(CH_2)_2SiCl_3$, $CF_3(CF_2)_7(CH_2)_2Si(OCH_3)_3$, $CF_3(CF_2)_7(CH_2)_2SiCl_3$, $CF_3(CF_2)_7(CH_2)_2SiCH_3Cl2$, $CF_3(CF_2)_7(CH_2)_2SiCH_3(OCH_3)_2$ etc. Other fluorocarbon substituted silicon compounds having at least one hydrolyzable group thereon are described in U.S. Pat. Nos. 2,993,925, 3,491,134, 4,652,663, 5,250,322 and 5,876,686, all incorporated herein by reference in their entirety. These fluorocarbon silicon compounds may be employed singly, in combination with each other or in combination with non-fluorinated sol-gel ceramic precursor compounds to form the ceramic sol employed in the invention.

Any hydrolysable alkoxysilane may be employed in combination with the fluoroalkylsilane. Examples of suitable alkoxysilanes include, but are not limited to, $Si(OC_2H_5)_4$, $Si(OCH_3)_4$, $CH_3Si(OCH_3)_3$, $Si(OC_2H_5)_3H$ and $Si(OC_3H_7)_4$. Alkoxysilanes with other reactive functionalities may also be employed in the fluorinated sol-gel ceramic formulation. Examples include glycidoxypropyltriethoxysilane (3-(2,3-epoxypropyloxy)propyltriethoxysilane), and methacryloxypropyltrimethoxysilane.

One method of sol formation is described in U.S. Pat. No. 5,250,322, which discloses the use of a hydrolysable fluoroalkylsilane mixed with a hydrolysable alkoxysilane. Using the method described in U.S. Pat. No. 5,250,322, a molar ratio of the alkoxysilane to the fluoroalkylsilane ranging from 1:10 to 10:1 is employed. The mixed solution is diluted with a solvent such that the total concentration of the alkoxysilane and the fluoroalkylsilane is from 1 to 10 wt % in a diluted solution, and water in an amount of 100 mol % to 1000 mol % of the total amounts of the fluoroalkylsilane and the alkoxysilane is added to the diluted solution so as to partially hydrolyze the fluoroalkylsilane and the alkoxysilane, thereby forming a sol.

Another example of producing a fluorinated sol-gel composite material uses at least one fluorinated inorganic oxide precursor in a fluorinated solvent with a fluorinated gelling agent to provide a sol that continues on to form a gel is disclosed in U.S. Pat. No. 5,876,686.

A method of making a fluoroalkyl-functional organosiloxane sol-gel is disclosed in U.S. Pat. No. 6,713,186, the entire content of which is incorporated by reference herein. The fluoroalkyl-functional organosilanes disclosed therein have the following general formula:

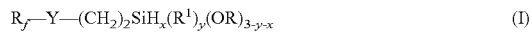

in which $R_f$ is a mono, oligo- or perfluorinated alkyl group having 1-18, and more suitably about 1-9 carbon atoms or a mono-, oligo- or perfluorinated aryl group, Y is a $CH_2$, O or S group, $R^1$ and R are each independently a linear, branched or cyclic alkyl group having 1-8 carbon atoms or an aryl group and x=0, 1 or 2 and y=0, 1 or 2, where (x+y)≦2. The composition is prepared by controlled hydrolysis at a temperature in the range of 0-120° C. over a period of 0.5-24 hours and with thorough mixing in an alcoholic medium which contains water, and a weak mono- or polybasic acid or a weak base or a weak mono- or polybasic acid and a weak base or an acid or basic salt, the water employed and the alkoxysilane employed being in a molar ratio of 2-500:1.

In one embodiment, at least one fluorocarbon functional organosilane having the following general formula is employed:

wherein R is an alkyl group having from 1-9 carbon atoms wherein at least the terminal carbon has at least one fluorine atom covalently bonded thereto or an aryl group having at least one fluorine atom covalently bonded thereto; $R_1$ is a $CH_2$—, $CH_2CH_2$—, or a functional group containing O, S, N or combination thereof and having a carbon atom covalently linked to —Si; $R_2$ is H, alkyl or a combination thereof; $R_3$ is a hydrolysable group; y is 0 or 1 and x is 0, 1 or 2. Examples of suitable hydrolysable groups include alkoxy, acyloxy, carboxy, and chlorine. Any groups attached through hydrolysable bonds may be employed, however. Most suitably, the hydrolysable group is an alkoxy group such as ethoxy or methoxy. Suitably, the terminal carbon atom of the fluorocarbon group R—(R$_1$)$_y$— has one, two or three fluorine atoms covalently bonded thereto, suitably at least two fluorine atoms covalently bonded thereto, preferably it has three fluorine atoms covalently bonded thereto. In some embodiments, R is a fluoroalkyl group having from 1-9 carbon atoms, with each carbon atom having two fluorine atoms covalently bonded thereto, and the terminal carbon atom having 3 fluorine atoms covalently bonded thereto.

Similar molecular structures of this type are disclosed in U.S. Pat. No. 5,459,198 and are as follows:

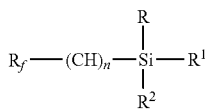

Wherein R$_f$ is as described above and R, R$^1$ and R$^2$ are as described above.

In another embodiment of a fluorocarbon functional silane of the formula (II), R$_2$ is ethoxy, x is 0, R$_1$ is CH$_2$CH$_2$— and R is a perfluorinated alkyl group having 6 carbon atoms. A commercial example of this compound is DYNASYLAN® F 8261, tridecafluoro-1,1,2,2-tetrahydrooctyltriethoxysi lane, available from Degussa, having the following chemical formula:

$$F_3C(CF_2)_5(CH_2)_2Si(OCH_3)_3$$

Other examples of a fluorinated silane that may be employed in formation of the sol-gel ceramic network and that come within the definition of formula (II) (taking R$_1$ as a functional group containing O, S, N or combination thereof and having a carbon atom covalently linked to —Si) are perfluoroalkylsulfonyl alkyl trialkoxysilanes, such as one having the chemical formula, C$_8$F$_{17}$SO$_2$NHC$_3$H$_6$Si(OCH$_3$)$_3$. This perfluoroalkylsulfonyl alkyl trialkoxysilane is commercially available from WYR Chemical Co., China, under the trade designation of FC-922.

The above examples of metal alkoxides which may be employed in the present invention are intended for illustrative purposes only, and not as a limitation on the scope of the present invention.

Further descriptions of fluorinated silanes that may be employed in the inventive polymer/fluorinated sol-gel ceramic composites of the invention is provided in "Preparation of Super-Water-Repellent Fluorinated Inorganic-Organic Coating Films on Nylon 66 by the Sol-Gel Method Using Microphase Separation," Satoh, K. et al., Journal of Sol-Gel Science and Technology, 27 (2003) 327-332; "Hybrid Organic-Inorganic Gels Containing Perfluoro-Alkyl Moieties," Ameduri, Bruno, et al., Journal of Fluorine Chemistry, 104 (2000) 185-194; "Preparation and Surface Properties of Silica-Gel Coating Films Containing Branched-Polyfluoroalkylsilane," Monde, Takashi, et al., Journal of Non-Crystalline Solids, 246 (1999) 54-64; "Hydrolysis and Condensation of Fluorine Containing Organosilicon, Kim," Jae-Pil, et al., Optical Materials, 21 (2002) 445-450; "Synthesis and Surface Antimicrobial Activity of a Novel Perfluorooctylated Quaternary Ammonium Silane Coupling Agent," Shao, Hui, et al., Journal of Fluorine Chemistry, 125 (2004) 721-724; "End-Capped Fluoroalkyl-Functional Silanes. Part II: Modification of Polymers and Possibility of Multifunctional Silanes," Kawase, Tokuzo, et al., J. Adhesion Sci. Technol., Vol. 16, No. 8, pp. 1121-1140 (2002); "End-Capped Fluoroalkyl-Functional Silanes. Part I: Modification of Glass," Kawase, Tokuzo, et al., J. Adhesion Sci. Technol., Vol. 16, No. 8, pp. 1103-1120 (2002) "A New Approach to Molecular Devices Using SAMs, LSMCD and Cat-CVD," Nishikawa, T. et al., Science and Technology of Advanced Materials, 4 (2003) 81-89, all of which are incorporated by reference herein in their entirety.

In forming the sol-gel ceramic, fluorocarbon-substituted silanes may be used alone if they contain an average of more than two hydrolyzable groups capable of self hydrolysis and self condensation, for instance alkoxy, acyloxy or chloro groups. However, in most cases, a fluorocarbon—and hydrolysable group—substituted silane is mixed with other hydrolysable silanes that contain hydrolysable groups, and suitably contain three or four hydrolyzable groups, for instance tetraethoxysilane, methyltrimethoxysilane or methyltriethoxysilane. In some embodiments hydrolysable silanes having other reactive functionalities, such as epoxy or (meth) acrylic groups, may be employed. Specific examples of such reactive silanes are methacryloxypropyltrimethoxysilane, and glycidoxypropyltriethoxysilane. The mixture is hydrolyzed and co-condensed.

In some embodiments, fluoroalkoxide complexes may be employed. Examples of such complexes are described in "Alkaline-earth metal fluoroalkoxide complexes with multi-coordinated polyether appendage: synthesis and characterization, Yun Chi et al., Inorganica Chimica Acta 334, 172-182 (2002).

In one aspect of the invention, a fluorinated sol-gel network of the type shown above is employed in combination with a polymer to form a composite region for a medical device. The composite is thus a hybrid material that includes polymer and ceramic. Polymers may be employed in combination with any of the sol-gel ceramics described above. The polymer may be mixed in solution before, during or after formation of the sol-gel composition. In some cases the polymer may be formed in situ with the sol-gel.

For example, the composite regions can contain bi-continuous polymeric and ceramic phases, domains of a ceramic phase may be dispersed in a polymer matrix, domains of a polymer phase may be dispersed in domains of a ceramic matrix. In some embodiments the best material properties are obtained when the polymer and ceramic are present in bi-continuous phases, that is, where the ceramic and polymer networks interpenetrate, apparently to the molecular level, so that separate domains are not observed under field emission microscopy or even under transmission electron microscopy. When a separate dispersed phase is present, it desirably will be of nanoscale dimension by which is meant that at least one cross-sectional dimension of the dispersed phase (e.g., the diameter for a spherical or cylindrical phase, the thickness for a ribbon- or plate-shaped phase, etc.) is less than 1 micron (1000 nm), for instance in the range of 0.1 nm to 500 nm, 0.25 nm to 100 nm, 0.5 nm to 20 nm, or 1-10 nm. A decrease in such dimensions generally results in an increase in the interfacial area that exists between the polymeric and ceramic phases.

In some cases multiple polymer and/or ceramic phases may be present. For example, multiple polymer phases may exist where the composite region contains a block copolymer or a blend of different polymers.

Any polymeric material may be incorporated into the sol-gel composite according to the invention. Elastomeric and non-elastomeric polymers may be employed. Examples of suitable polymeric materials include, but are not limited to, polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers of the above. In accordance with some embodiments of the invention the polymer is an organic polymer or an organic polymer modified with M(OR)$_x$ groups where M and R are as defined subsequently herein.

In some embodiments, a fluorinated sol-gel network of the type described above is employed in combination with at least one thermoplastic block copolymer. The thermoplastic block copolymer may be a polyamide-block-ether block copolymer such as a PEBAX® polymer, a polyether-block-ester copolymer such as those available from DuPont in Wilmington, Del., under the tradename of HYTREL®, at least one copolyester which is a polyester-block-ester, or at least one thermoplastic polyurethane block copolymer.

In preparing the hybrid inorganic-organic sol-gel material, the polymer may be dissolved in a suitable solvent such as an alcohol or alcohol mixture. This may require mixing and/or reflux, as well as elevated temperatures. Fluorinated solvents may be desirable in some instances.

In some embodiments, the temperature of reflux is suitably about 60° C. to about 80° C., and vigorous stirring over a period of about 2 to about 6 hours. The polymer may be added to the solvent or solvent mixture at a concentration of about 0.1% to about 10% by weight. The sol-gel precursors may then be added to the same solvent or solvent mixture as the polymer. The sol-gel precursors may also be dissolved prior to mixing with the polymer. Stoichiometric amounts of water, diluted mineral acid such as hydrochloric acid, or acetic acid at a pH of about 2-3, may be added drop-wise with stirring. The resultant mix can be aged at room temperature or at slightly elevated temperatures of about 50° C. to about 60° C. under ambient conditions for about 5 to about 10 hours. Ratios of polymer to sol-gel precursors may range from about 80:20 to about 20:80.

After aging, the solvent/polymer/sol-gel mixture can be used to coat any medical device or component thereof. This can be accomplished by spraying, dipping, brushing, painting, syringe injection, or any other coating method known in the art. Dipping of a medical device or component in the solution, allows for easy access to inner surfaces not otherwise easily coated. For example, inner surfaces of catheter shafts, which are quite small, are difficult to reach. Syringe injection may also be employed for inner surfaces.

The medical device or component thereof may then be allowed to dry at room temperature, at elevated temperatures and/or under vacuum.

The above procedure is intended for illustrative purposes only. Different solvents, temperatures, catalysts, mix times, ratios employed, or other procedural steps may be varied depending on the polymers, sol-gel precursors, or other fluorinated species selected for use.

The polymer may also be formed in situ. An illustrative preparation of an inorganic-organic composite material of polymethylmethacrylate and an acrylic and fluorocarbon functionalized siloxane network is disclosed in "Preparation and characterization of hydrophobic organic-inorganic composite thin films of PMMA/SiO$_2$/TiO$_2$ with low friction coefficient," Gu, Guotuan, et al., *Applied Surface Science*, 221

(2004) 129-135. The precursor solution of this hybrid system is based on 3-methacryloxypropyltrimethoxysilane, tetramethyloxysilane, methyl methacrylate, a fluoroperfluroalkysulfonylalkyltrialkoxysilane and tetrabutyl titanate. The methacrylate polymer resulting from this process is crosslinked with the ceramic network.

The lubriciousness of the polymer/fluorinated sol-gel ceramic composite material of the invention can of course be varied by varying the number of fluorocarbon groups incorporated into the composite, as well as the length of the fluorocarbon chain which is employed in the sol-gel derived ceramic.

Therapeutic agent(s) may also be incorporated in the sol-gel derived composite material according to the invention. The therapeutic agent may be disposed within or beneath the composite material, in which cases the composite regions may be referred to as carrier regions or barrier regions. By "composite carrier region" is meant a region of composite material which further comprises a therapeutic agent and from which the therapeutic agent is released. By "composite barrier region" is meant a region of composite material which is disposed between a source of therapeutic agent and a site of intended release, and which controls the rate at which therapeutic agent is released. For example, in some embodiments, the medical device includes a composite barrier region that surrounds a source of therapeutic agent. In other embodiments, the composite barrier region is disposed over a source of therapeutic agent, which is in turn disposed over all or a portion of a medical device substrate.

"Therapeutic agents," "drugs," "pharmaceutically active agents," "pharmaceutically active materials," and other related terms are employed in the art interchangeably. Hereinafter, the term therapeutic agent will be employed herein. Therapeutic agents include genetic materials, non-genetic materials, and cells.

Examples of non-genetic therapeutic agents include, but are not limited to, anti-thrombogenic agents, anti-proliferative agents, anti-inflammatory agents, analgesics, antineoplastic/antiproliferative/anti-miotic agents, anesthetic agents, anti-coagulants, vascular cell growth promoters, vascular cell growth inhibitors, cholesterol-lowering agents; vasodilating agents; and agents which interfere with endogenous vasoactive mechanisms.

Of course mixtures of any of the above may also be employed.

The above lists are intended for illustrative purposes only, and not as a limitation on the scope of the present invention.

Therapeutic agents are discussed in commonly assigned U.S. Patent Application 2004/0215169 and U.S. Pat. No. 6,855,770, each of which is incorporated by reference herein in its entirety.

When used to form a "composite carrier region" or a "composite barrier region," the hydrophobicity imparted by the fluorocarbon groups in the ceramic network allows for the delivery rate of many therapeutic agents to be fine tuned by altering the relative amount of fluorination in the ceramic and the ratio of ceramic to polymer in the composite material.

Although the invention has been described primarily in the context of a coating for providing surface lubricity, or reduced coefficient of friction, in another embodiment the composite materials of the invention may be employed as a tie layer between a substrate and a fluorocarbon polymer coating material to improve the bond strength of the coating. In still another embodiment the composite material may be a bulk material from which a medical device part is formed, for instance by molding or casting the polymer/sol mixture and then heating and drying to form the composite material, or by machining from a sheet, rod, bar or other stock form of the composite material.

The embodiments described above are intended to be illustrative of the present invention and are not intended to limit the scope of the invention in any way. The following non-limiting examples further illustrate the present invention.

EXAMPLES

Examples 1 and 2

A hybrid inorganic-organic sol-gel material was prepared using DYNASYLAN® F8261, tridecafluoro-1,1,2,2-tetrahydrooctyltriethoxysilane, available from Degussa in Dusseldorf, Germany, as the sol-gel precursor component. PEBAX® 2533, 0.8 grams, was dissolved in 28 g of 1-butanol and 12 g of 1-propanol, under reflux, near the boiling point of the butanol/propanol mixture. Once the PEBAX® was sufficiently dissolved, the mixture was allowed to cool and the DYNASYLAN® F8261 was added in various amounts from 1 wt-% to 20 wt-%, as shown in Table 1, below. A stoichiometric amount of hydrochloric acid, 0.15M, was then added.

For example, a mixture of 2 wt-% PEBAX® 2533 and 2 wt-% DYNASYLAN® F8261, 2 wt-% PEBAX® 2533 and 4 wt-% DYNASYLAN® F8261, had the following ingredients:

| Example 1 | Example 2 |
|---|---|
| 28 g 1-Butanol | 28 g 1-Butanol |
| 12 g 1-Propanol | 12 g 1-Propanol |
| 0.8 g PEBAX ® 2533 | 0.8 g PEBAX ® 2533 |
| 0.8 g DYNASYLAN ® F8261 | 1.6 g DYNASYLAN ® F8261 |
| 0.056 g 0.15M HCl | 0.056 g 0.15M HCl |

This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A medical device, the medical device is insertable or implantable in a patient's body and is a member selected from the group consisting of catheter assemblies, stent delivery assemblies, medical balloons, stents, grafts, stent-grafts, embolization devices, guide wires, needles, surgical instruments, endoscopic equipment, myocardial plugs, wound drains, gastroenteric tubes, urethral inserts, laproscopic equipments, pacemaker leads, defibrillator leads and shunts, the medical device having at least a region thereon formed of composite material, the composite material is formed from a hybrid organic-inorganic material that includes a polymer and a fluorinated sol-gel derived ceramic, the fluorinated sol-gel derived ceramic is formed from at least one hydrolysable network-forming fluorinated metal compound which is a fluorinated metal alkoxide comprising at least one mono-, oligo- or perfluorinated alkyl or aryl group which is linked to the metal via a carbon-metal bond which is not subject to hydrolysis and at least two network-forming groups, the metal comprises at least one member selected from the group consisting of silicon, tin, aluminum, hafnium, titanium, zirconium, tantalum, molybdenum, tungsten, rhenium, iridium, an alkaline earth metal and a rare earth lanthanide.

2. The medical device of claim 1 wherein said metal comprises silicon.

3. The medical device of claim 1 wherein the fluorinated sol-gel derived ceramic is formed from at least one metal alkoxide and at least one fluoroalkylsilane.

4. The medical device of claim 1 wherein said fluorinated sol-gel derived ceramic is formed from at least one sol-gel precursor compound which is a fluorinated silane having at least one fluorocarbon containing group and at least one hydrolysable group thereon.

5. The medical device of claim 4 wherein said fluorinated silane is a fluoroalkylalkoxysilane.

6. The medical device of claim 4 wherein said fluorinated silane is a fluoroalkylfunctional organosilane with the following general formula:

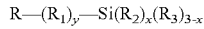

wherein R is an alkyl group having from 1-9 carbon atoms wherein at least the terminal carbon atom has one or more fluorine atoms covalently bonded thereto or an aryl group having at least one fluorine atom covalently bonded thereto; $R_1$ is a $CH_2$—, $CH_2CH_2$—, or a functional group containing O, S, N or combination thereof and having a carbon atom covalently linked to —Si; $R_2$ is H, alkyl or a combination thereof; $R_3$ is a hydrolysable group; y is 0 or 1 and x is 0, 1 or 2.

7. The medical device of claim 6 wherein R is an alkyl group having from 1-9 carbon atoms wherein at least the terminal carbon atom has three fluorine atoms covalently bonded thereto.

8. The medical device of claim 6 wherein R is an alkyl group having from 4-8 carbon atoms, and each carbon atom having two fluorine groups covalently bonded thereto and the terminal carbon atom having three fluorine groups covalently bonded thereto.

9. The medical device of claim 8 wherein $R_3$ is alkoxy, acyloxy or chlorine.

10. The medical device of claim 8 wherein $R_3$ is ethoxy, x is 0, y is 1, $R_1$ is $CH_2CH_2$— and R is a perfluorinated alkyl group having 6 carbon atoms.

11. The medical device of claim 4 wherein said fluorinated silane is $CF_3(CH_2)_2Si(OCH_3)_3$, $CF_3(CH_2)_2SiCl_3$, $CF_3(CF_2)_5(CH_2)_2Si(OCH_3)_3$, $CF_3(CF_2)_5(CH_2)_2SiCl_3$, $CF_3(CF_2)_7(CH_2)_2Si(OCH_3)_3$, $CF_3(CF_2)_7(CH_2)_2SiCl_3$, $CF_3(CF_2)_7(CH_2)_2SiCH_3Cl2$, $CF_3(CF_2)_7(CH_2)_2SiCH_3(OCH_3)_2$, $C_8F_{17}SO_2NHC_3H_6Si(OCH_3)_3$, or a mixture of two or more thereof.

12. The medical device of claim 1 wherein said polymer is an organic polymer.

13. A medical device as in claim 12 wherein the organic polymer has a plurality of hydroxyl, amide, carboxylic acid, ester or ether groups thereon.

14. A medical device as in claim 12 wherein the organic polymer comprises segments of polyamide or polyether or both.

15. A medical device as in claim 1 wherein said composite material comprises covalent linkages between said polymer and said sol-gel derived ceramic.

16. A medical device as in claim 15 wherein said covalent linkages comprise carbon-linked organosilicon groups.

17. A medical device as in claim 1 wherein said sol-gel derived ceramic and said polymer, respectively, form interpenetrating networks within the composite material.

18. The medical device of claim 1 wherein in the composite material the polymer and a fluorinated sol-gel derived ceramic are present in separate phases or in bi-continuous phases, or both.

19. The medical device of claim 1 wherein said medical device is an implantable or insertable medical device.

20. The medical device of claim 1 wherein the medical device is selected from a catheter, a balloon, a guide wire, a vena cava filter, a stent, a stent graft, a vascular graft, a cerebral aneurysm filler coil, a myocardial plug, a heart valve, a vascular valve, and a tissue engineering scaffold.

21. The medical device of claim 1 wherein the medical device is a delivery catheter having an inner shaft and an outer shaft, at least the inner shaft comprising said region comprising said composite material.

22. The medical device of claim 1 wherein said composite material further comprises at least one therapeutic agent.

23. The medical device of claim 1 wherein said composite material is disposed between a source of therapeutic agent and a site of intended release, and which controls the rate at which therapeutic agent is released.

24. A catheter assembly, at least a portion of the catheter assembly having disposed on a surface thereof a composite material comprising a polymer and a fluorinated sol-gel derived ceramic, the fluorinated sol-gel derived ceramic is formed from at least one hydrolysable network-forming fluorinated metal compound which is a fluorinated metal alkoxide comprising at least one mono-, oligo- or perfluorinated alkyl or aryl group which is linked to the metal via a carbon-metal bond which is not subject to hydrolysis and at least two network-forming groups, the metal comprises at least one member selected from the group consisting of silicon, tin, aluminum, hafnium, titanium, zirconium, tantalum, molybdenum, tungsten, rhenium, iridium, an alkaline earth metal and a rare earth lanthanide.

25. An expandable medical balloon, the expandable medical balloon having an inner surface and an outer surface, the expandable medical balloon comprising a composite barrier region on at least a portion of the outer surface, the composite barrier region is formed of a composite material comprising a polymer and a fluorinated sol-gel derived ceramic, the fluorinated sol-gel derived ceramic is formed from at least one hydrolysable network-forming fluorinated metal compound which is a fluorinated metal alkoxide comprising at least one mono-, oligo- or perfluorinated alkyl or aryl group which is linked to the metal via a carbon-metal bond which is not subject to hydrolysis and at least two network-forming groups, the metal comprises at least one member selected from the group consisting of silicon tin aluminum, hafnium, titanium, zirconium, tantalum, molybdenum, tungsten, rhenium, iridium, an alkaline earth metal and a rare earth lanthanide.

26. The catheter assembly of claim 24, the catheter assembly comprising at least one expandable balloon member, at least a portion of said expandable balloon member comprising said composite material.

27. The catheter assembly of claim 26 wherein said composite material further comprises at least one therapeutic agent.

28. The catheter assembly of claim 24 comprising at least one catheter shaft, the catheter shaft having an inner surface forming a guide wire lumen, the inner surface of the catheter shaft comprising said composite material.

* * * * *